(12) United States Patent
Doshi et al.

(10) Patent No.: US 9,526,812 B2
(45) Date of Patent: Dec. 27, 2016

(54) BIODEGRADABLE MEDICAL DEVICES AND METHOD TO CONTROL DEGRADATION OF THE BIODEGRADABLE MEDICAL DEVICES

(75) Inventors: Manish Doshi, Surat (IN); Pankaj Gandhi, Surat (IN); Ronak Choksi, Surat (IN); Prakash Sojitra, Surat (IN)

(73) Assignee: ENVISION SCIENTIFIC PRIVATE LIMITED, Surat (IN)

( * ) Notice: Subject to any disclaimer, the term of this patent is extended or adjusted under 35 U.S.C. 154(b) by 387 days.

(21) Appl. No.: 13/979,352

(22) PCT Filed: Jan. 10, 2012

(86) PCT No.: PCT/IN2012/000027
§ 371 (c)(1),
(2), (4) Date: Dec. 26, 2013

(87) PCT Pub. No.: WO2012/095865
PCT Pub. Date: Jul. 19, 2012

(65) Prior Publication Data
US 2014/0107615 A1    Apr. 17, 2014

(30) Foreign Application Priority Data
Jan. 11, 2011    (IN) .......................... 2815/MUM/2010

(51) Int. Cl.
*A61F 2/06*    (2013.01)
*A61L 29/08*    (2006.01)
(Continued)

(52) U.S. Cl.
CPC .................. *A61L 29/08* (2013.01); *A61F 2/82* (2013.01); *A61L 27/34* (2013.01); *A61L 27/54* (2013.01); *A61L 27/58* (2013.01); *A61L 29/085* (2013.01); *A61L 29/148* (2013.01); *A61L 29/16* (2013.01); *A61L 31/10* (2013.01); *A61L 31/148* (2013.01); *A61L 31/16* (2013.01);
(Continued)

(58) Field of Classification Search
CPC ............... A61F 2210/0004; A61F 2250/003; A61F 2250/0067; A61L 2300/606; A61L 2300/608; A61L 27/34; A61L 27/54; A61L 27/58; A61L 29/08; A61L 29/085; A61L 29/148; A61L 29/16; A61L 31/10; A61L 31/148; A61L 31/16
USPC ..................................... 623/1.44, 1.45, 1.32
See application file for complete search history.

(56) References Cited

U.S. PATENT DOCUMENTS 8,808,726 B2 *  8/2014  Atanasoska ............. A61L 31/10
                                                                        424/426

* cited by examiner

*Primary Examiner* — Kevin C Sirmons
*Assistant Examiner* — Deanna K Hall
(74) *Attorney, Agent, or Firm* — Timberline Patent Law Group PLLC

(57) ABSTRACT

An implantable biodegradable device having two or more layers composed of one or more biodegradable materials is disclosed. The two or more layers are coated with one or more drugs. The implantable biodegradable device further having one or more inert layers is composed of a biodegradable material. The one or more inert layers of the implantable biodegradable device are degraded in response to introduction of one or more external triggers when the implantable biodegradable medical device is placed within a living organism. Further, a layer of the two or more layers having a position above an inert layer is degraded prior to degradation of the inert layer. Subsequently, a layer of the two or more layers having a position below the inert layer is degraded subsequent to degradation of the inert layer.

18 Claims, 2 Drawing Sheets

(51) Int. Cl.
*A61F 2/82* (2013.01)
*A61L 27/34* (2006.01)
*A61L 27/54* (2006.01)
*A61L 27/58* (2006.01)
*A61L 29/14* (2006.01)
*A61L 29/16* (2006.01)
*A61L 31/10* (2006.01)
*A61L 31/14* (2006.01)
*A61L 31/16* (2006.01)

(52) U.S. Cl.
CPC . *A61F 2210/0004* (2013.01); *A61F 2250/003* (2013.01); *A61F 2250/0067* (2013.01); *A61L 2300/606* (2013.01); *A61L 2300/608* (2013.01)

BIODEGRADABLE MEDICAL DEVICES AND METHOD TO CONTROL DEGRADATION OF THE BIODEGRADABLE MEDICAL DEVICES

RELATED APPLICATIONS

This patent application claims the benefit of priority to International PCT Application No. PCTIN2012000027, filed Jan. 10, 2012, which in turn claims the benefit of priority to India Patent Application No. 2815MUM2010, filed Jan. 11, 2011, both of these incorporated by reference herein in their entireties.

FIELD OF THE INVENTION

The invention generally relates to biodegradable medical devices and a method to control degradation of the biodegradable medical devices in-vivo.

BACKGROUND OF THE INVENTION

Generally, non-biodegradable implantable medical devices, such as, a metallic stent, remains in a patient's body throughout the life of the patient. Such medical devices being exogenous to the body may cause untoward reactions in the body. Such medical devices may also pose problem during interventional procedures. For example, a metallic stent implanted in the body of a patient may pose problems during coronary artery bypass surgery, diagnosis using magnetic resonance imaging, computed tomography scan and the like. To overcome the problems associated with the non-biodegradable medical devices, biodegradable implantable medical devices are used.

The biodegradable implantable medical devices remain in the body of a patient for a particular time and then degrade eventually. Thus, after the particular time no biodegradable medical devices remain in the body of a patient. For example, biodegradable stent may degrade over a period between 3 months to 3 years and then there is no implant in the body.

However, rigidity and force offered by the biodegradable medical devices to a body organ may not sustain for a desired period because of continuous and uncontrolled degradation of the biodegradable medical devices. For example, degradation of a biodegradable stent may start from first day of implanting such stent thereby eventually resulting in reduction of radial force and rigidity offered by such stent to the vessels. Thus, continuous and uncontrolled degradation of such stent weakens the strength of stent to hold artery against arterial pressure.

Therefore, there is a need in the art for biodegradable medical devices exhibiting controlled degradation in-vivo and a method to control degradation of the biodegradable medical devices.

BRIEF DESCRIPTION OF FIGURES

The accompanying figures where like reference numerals refer to identical or functionally similar elements throughout the separate views and which together with the description below are incorporated in and form part of the provisional specification, serve to further illustrate various embodiments and to explain various principles and advantages all in accordance with the invention.

DETAILED DESCRIPTION OF THE INVENTION

Before describing in detail embodiments that are in accordance with the invention, it should be observed that the embodiments reside primarily in a method for controlling degradation of the biodegradable medical devices in-vivo. Accordingly, the apparatus components and the method steps have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Further, before describing in detail embodiments that are in accordance with the invention, it should be observed that all the scientific and technical terms used in for describing the invention have same meanings as would be understood by a person skilled in the art.

Various embodiments of the invention provide an implantable biodegradable device having two or more layers composed of one or more biodegradable materials. The two or more layers are coated with one or more drugs. The implantable biodegradable device further includes one or more inert layers. The one or more inert layers are composed of a biodegradable material. The one or more inert layers of the implantable biodegradable device are degraded in response to introduction of one or more external triggers when the implantable biodegradable medical device is placed within a living organism. As the one or more layers gets degraded, a layer of the two or more layers having a position above an inert layer is degraded prior to degradation of the inert layer. Similarly, a layer of the two or more layers having a position below the inert layer is degraded subsequent to degradation of the inert layer.

Figure 1:
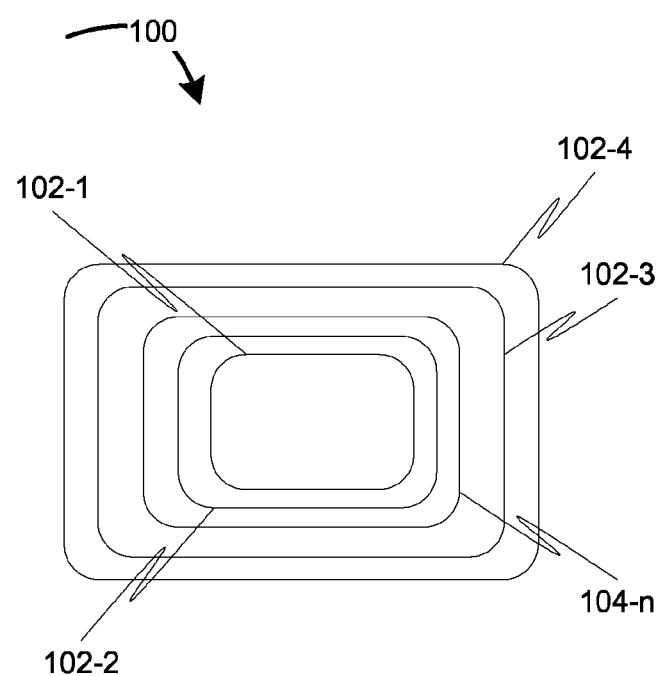
FIG. 1 illustrates a cross-sectional view of an implantable biodegradable medical device 100 in accordance with an embodiment of the invention.

FIG. 1 illustrates a cross-sectional view of an implantable biodegradable medical device 100. Examples of implantable biodegradable medical device 100 may include but are not limited to, a stent, a spinal implant, a dental implant, an osteo-implant, sutures, an ear implant, a throat implant, an orthopedic implant, and a prosthesis. Implantable biodegradable medical device 100 includes two or more layers 102-n, such as layer 102-1, layer 102-2, layer 102-3, and layer 102-4 composed of one or more biodegradable materials.

The one or more biodegradable materials are selected from a polymer, a co-polymer, a homopolymer, an ester, an anhydride, an orthoster, an amide, a polyester, biodegradable linear aliphatic polyesters, biodegradable copolymers between linear aliphatic polyesters, Polyanhydrides, Poly (Othoesters), Poly(Ester-Ethers), biodegradable Polysaccharides, and Polyamino Acids, inorganic biodegradable polymers. Examples of one or more biodegradable material include but are not limited to, polyesters composed of homopolymers or co-polymers of glycolide and lactide; co-polymers of trimethylene carbonate, e-caprolactone and polydiaxanone; and Poly Glycolic Acid (PGA), Poly(Lactic-co-Glycolic Acid) (PLGA), Poly(Ethylene Glycol) (PEG), Polyglactin, Polyglyconate, Polydiaxanone, Polyglecaprone, Polyglycolide, Polylactide, Polyhydroxybutyrate, Poly(Glycolide-E-Caprolactone), Poly(Glycolide Trimethylene Carbonate), Poly(L-lactic Acide-L-lysine) copolymer, Tyrosine-based polyarylates, Polyiminocarbonates, Polycarbonates, Poly(D,L-lactide-Urethane), Poly(esteramide), Poly-P-Dioxanone, hyaluronic acid, chitin, chitosan, Poly-L-Glutamic Acid, Poly-L-Lysine, Polyphosphazene and Poly[bis(carboxylatophenoxy)phosphazene].

In an embodiment, two or more layers 102-$n$ have a varying thickness ranging from 50 micron to 200 micron. Two or more layers 102-$n$ are coated with one or more drugs for treating the living organism.

Implantable biodegradable medical device 100 further includes one or more inert layers 104-$n$ such as an inert layer 104-1. In an embodiment, one or more inert layers 104-$n$ of implantable biodegradable medical device 100 have a thickness ranging from 2 micron to 50 micron. Examples of one or more inert layers 104-$n$ include but are not limited to, oleic acid, lauric acid, bile acid, amino acid, cholic acid and uric acid. One or more inert layers 104-$n$ are coated with one or more drugs for treating the living organism.

The one or more drugs coated on one or more of two or more layers 102-$n$ and one or more inert layers 104-$n$ may be selected from an anti-inflammatory agent, an anti-thrombotic agent, an anti-proliferative agent, estrogens, a thrombolytic agent, an antimitotic, a smooth muscle cell inhibitor, a fibrinolytic, a anti-antigenic agent, a healing promoter, an antibiotic, a protease inhibitor, one or more antibodies, an anti-mitotic agent, an immunosuppressive agent, a cytostatic agent, a cytotoxic agent, a calcium channel blocker, an antioxidant and an anti-platelet aggregating agent. Examples of one or more drugs include but are not limited to, paclitaxel, sirolimus, analogs of mitomycin, dexamethasone, genestine, flavenoids like flavanones, neoflavones, aurones, chalcones, dihydrochalcones, flavonols, dihydroflavonols, flavones, flavanols, isoflavones, anthocyanidins, proanthocyanidins, isoflavanes, heparin, beta-estradiol, and analogs rapamycin, everolimus, biolimus, zotarolimus.

As shown in FIG. 1, two or more layers 102-$n$ and one or more inert layers 104-$n$ are positioned relative to each other. Referring back to FIG. 1, layer 102-4 is positioned above layer 102-3, followed by inert layer 104-1. Similarly, layer 102-2 is positioned below inert layer 104-1 followed by layer 102-1. In an embodiment, one or more inert layers 104-$n$ may be positioned above layer 102-3 and below layer 102-2. In an exemplary embodiment, implantable biodegradable medical 100 may have one or more inert layers 104-$n$ such as inert layer 104-1, an inert layer 104-2, and an inert layer 104-3. Inert layer 104-1 may be positioned above layer 102-1, inert layer 104-2 may be positioned above layer 102-2 and inert layer 104-3 may be positioned above layer 102-3.

Once implantable medical device 100 is positioned at a target site within the living organism, two or more layers 102-$n$ and one or more inert layers 104-$n$ starts degrading relative to each other. A layer of two or more layers 102-$n$ having a position above inert layer 104-1 is degraded prior to degradation of inert layer 104-1 when placed at the target site within a living organism. As shown in FIG. 1, layer 102-4 composed of the one or more biodegradable materials, degrades first on coming in contact with body fluids of the living organism. In response to degradation of layer 102-4, the one or more drugs are immediately released within the living organism. The one or more drugs released from layer 102-4 provide immediate relief at the target site. After, degradation of layer 102-4, layer 102-3 is exposed to the body fluids of the living organism. Here, layer 102-4 degrades faster than layer 102-3. The degradation of layer 102-3 may be delayed based on the one or more biodegradable materials the layer 102-3 is composed of The one or more biodegradable materials have a glass transition temperature ranging from 30° C. to 120° C. A layer of two or more layers 102-$n$ degrade based on a glass transition temperature associated with one or more biodegradable materials composing the layer. Layer 102-3 is composed of the one or more biodegradable materials having a degradation rate of 1 day to 60 days. As the degradation of layer 102-3 progresses, the one or more drugs are released. The one or more drugs are targeted to treat in-tissue injury due to positioning of implantable biodegradable medical device 100 at the target site within the living organism.

Thereafter, inert layer 1 is exposed to the body fluids of the living organism. Inert layer 104-1 aids in maintaining rigidity and force of implantable biodegradable medical device 100 at the target site even after the degradation of layer 102-4 and layer 102-3. Inert layer 104-1 is degraded to release the one or more drugs on introduction of one or more external triggers at the target site within the living organism. The one or more drugs are released at the target site when one or more inert layers 104-$n$ is exposed to body fluids of the living organism. Alternatively, the one or more drugs are released when one or more inert layers 104-$n$ are mechanically broken down using one or more external triggers. The one or more external triggers include, but are not limited to, one or more chemical agents and one or more non-implantable medical devices.

In an embodiment, when the one or more external triggers include one or more chemical agents, the amount of the one or more chemical agents required for degradation of one or more inert layers 104-$n$ ranges from 45 mcg to 500 mcg. The duration of degradation of one or more inert layers 104-$n$ in response to the introduction of the one or more chemical agents ranges from one day to 365 days. Examples of the one or more chemical agents include but are not limited to, stearic acid, sebesic acid, mannuronic acid, cationic derivatives of biocompatible hyaluronic acids, olic acid, and lauric acid.

In another embodiment, the one or more drugs are released when one or more inert layers 104-$n$ are degraded mechanically using one or more non-implantable medical devices. Examples of the non-implantable medical device include but are not limited to, a balloon, a catheter, a Percutaneous Transluminal Angioplasty (PTA) catheter and a Percutaneous Transluminal Coronary Angioplasty (PTCA) catheter. In an exemplary embodiment, a non-implantable device is a balloon. The balloon may be introduced to one or more inert layers 104-$n$ in a deflated state. Upon reaching one or more inert layers 104-$n$, the balloon is inflated causing mechanical breakdown of one or more inert layers 104-$n$. Thereafter, one or more drugs may be released from one or more inert layers 104-$n$.

Thereafter, layer 104-2 positioned below inert layer 104-1 is exposed to the body fluids of the living organism and degraded subsequent to degradation of inert layer 104-1. Layer 102-2 degrades prior to layer 104-1 releasing the one or more drugs and exposes layer 102-1 to the body fluids of the living organism. Similarly, upon degradation of layer 104-2 and layer 104-1 the one or more drugs are released from layer 104-2 and layer 104-1. The one or more drugs provide prolong treatment in the living organism. The one or more drugs may treat a later stage of a disease in the organism. Alternatively, the one or more drugs may prevent reoccurrence of the disease in the living organism. In an embodiment, layer 102-2 degrades prior to layer 102-1 because layer 102-2 has a higher glass transition temperature than layer 102-1.

Figure 2:
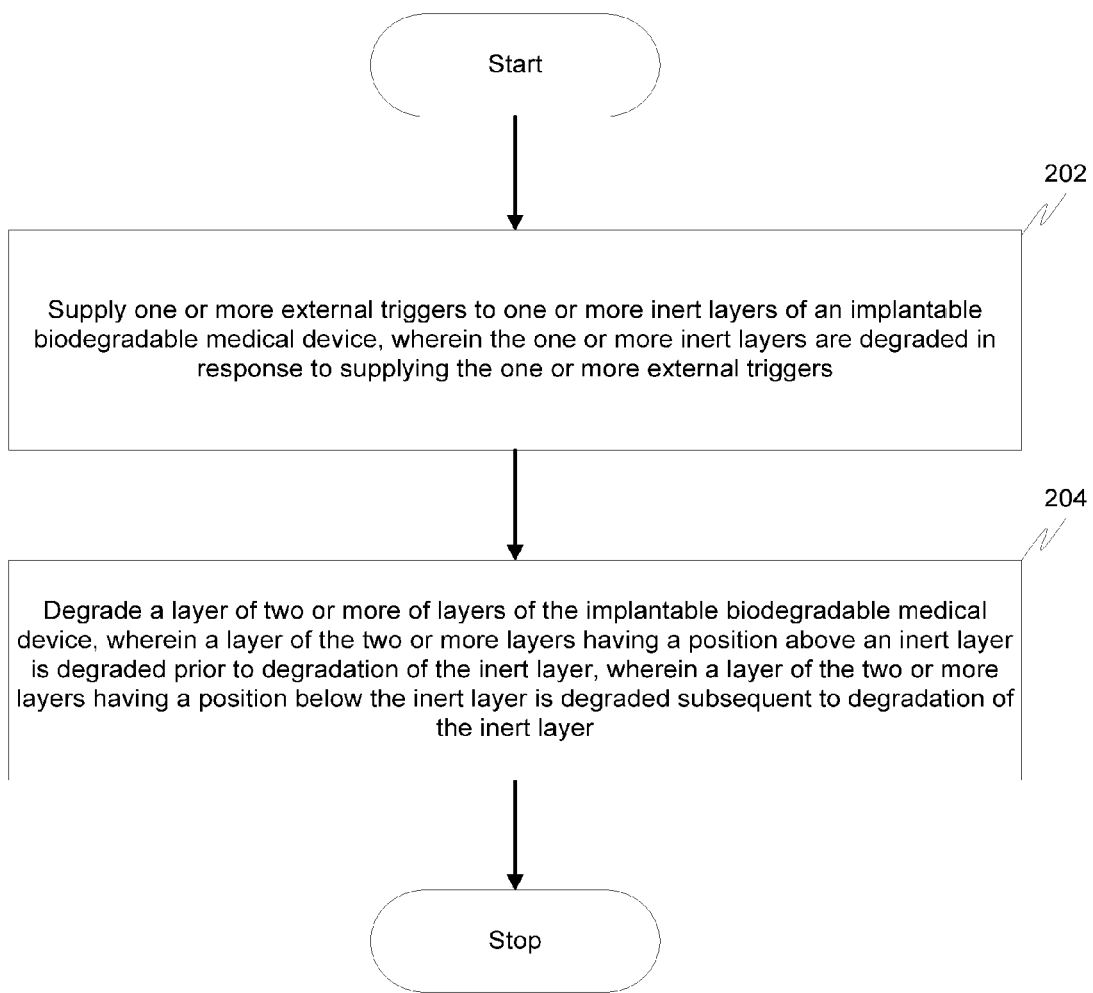
FIG. 2 illustrates a method of controlling degradation of an implantable biodegradable medical device placed within a living organism in accordance with an embodiment of the invention.

FIG. 2 illustrates a method of controlling degradation of an implantable biodegradable medical device placed within a living organism. The implantable biodegradable medical device includes two or more layers composed of one or more biodegradable materials. The two or more layers are coated with one or more drugs for treating a living organism. The implantable biodegradable medical device further includes one or more inert layers. The one or more inert layers are also coated with one or more drugs for treating the living organism. The two or more layers are positioned relative to the one or more inert layers as explained in conjunction with FIG. 1. The two or more layer have a position above and below the one or more inert layers.

At step 202, one or more external triggers are supplied to one or more inert layers of the implantable biodegradable medical device. Subsequently, the one or more inert layers are degraded in response to supplying of the one or more external triggers. At step 204, a layer of two or more layers of the implantable biodegradable medical device is degraded. The layer is positioned either above or below the one or more inert layers. Accordingly, the layer having a position above the one or more inert layers degrades prior to degradation of the one or more inert layers. Similarly, the layer of the plurality of layers having a position below the one or more inert layers degrades subsequent to degradation of the one or more inert layers caused by the one or more external triggers.

The one or more external triggers include but are not limited to one or more chemical agents and one or more non-implantable medical devices. The one or more external triggers are supplied the one or more inert layers by means of a balloon, a catheter, a PTA catheter and a PTCA catheter. The one or more external triggers cause the degradation of the one or more inert layers. The one or more drugs coated on the one or more inert layer are released in response to the degradation of the one or more inert layers. Further, the one or more drugs are released in response to degradation of the layer of the two or more layers. The two or more layers are degraded on coming in contact with body fluids. The two or more layers may have corresponding degradation rates associated with the one or more biodegradable material the two or more layers.

Various embodiments of the invention provide an implantable biodegradable medical device and a method to control degradation of the implantable biodegradable medical device. The invention also provides a method for controlling the initiation of the degradation of the biodegradable implantable medical devices thereby sustaining axial strength, radial rigidity and radial force of the biodegradable implantable medical devices for a time as a physician may deem adequate.

Those skilled in the art will realize that the above-recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes may be made to the invention without deviating from the scope of the invention. Accordingly, the specification is to be regarded in an illustrative rather than a restrictive sense, and all such modifications are intended to be included within the scope of the invention.

What is claimed is:

1. An implantable biodegradable medical device comprising:
   a rigid member in the implantable biodegradable medical device, the rigid member having an inner surface and an outer surface;
   at least one inert layer composing the rigid member, the at least one inert layer capable of providing an axial strength and a radial rigidity to the implantable biodegradable medical device;
   a plurality of layers on the outer surface of the rigid member composed of at least one biodegradable material, wherein the plurality of layers on the outer surface are coated with a corresponding at least one drug;
   a plurality of layers on the inner surface of the rigid member composed of at least one biodegradable material, wherein the plurality of layers on the inner surface are coated with a corresponding at least one drug;
   the at least one inert layer composed of a material not biodegradable unless triggered;
   wherein the at least one inert layer remains inert to provide the axial strength and the radial rigidity until the plurality of layers on the outer surface of the rigid member have degraded to release the corresponding at least one drug, thereby exposing the at least one inert layer, and wherein the at least one inert layer remains inert to provide the axial strength and the radial rigidity until a degradation of the at least one inert layer is initiated by at least one external trigger; and
   wherein the plurality of layers on the inner surface of the rigid member remain intact without releasing the corresponding at least one drug until the degradation of the at least one inert layer exposes the plurality of layers on the inner surface.

2. The implantable biodegradable medical device of claim 1, wherein the implantable biodegradable medical device is one of a stent, a spinal implant, a dental implant, an osteo-implant, sutures, an ear implant, a throat implant, an orthopedic implant, and a prosthesis.

3. The implantable biodegradable medical device of claim 1, wherein thickness of the at least one inert layer ranges from 2 micron to 50 micron.

4. The implantable biodegradable medical device of claim 1, wherein the at least one inert layer is coated with at least one drug.

5. The implantable biodegradable medical device of claim 1, wherein the biodegradable material present in the at least one inert layer is one of oleic acid, lauric acid, bile acid, amino acid, cholic acid and uric acid.

6. The implantable biodegradable medical device of claim 1, wherein the at least one external trigger comprises one of a chemical agent or a non-implantable medical device.

7. The implantable biodegradable medical device of claim 6, wherein the at least one chemical agent is selected from the group consisting of a stearic acid, a sebesic acid, a mannuronic acid, cationic derivatives of biocompatible hyaluronic acids, an olic acid, and a lauric acid.

8. The implantable biodegradable medical device of claim 6, wherein the at least one non-implantable medical device is selected from the group consisting of a balloon, a catheter, a Percutaneous Transluminal Angioplasty (PTA) catheter, and a Percutaneous Transluminal Coronary Angioplasty (PTCA) catheter.

9. The implantable biodegradable medical device of claim 7, wherein an amount of the chemical agent for degradation of the at least one inert layer ranges from 45 mcg-500 mcg.

10. The implantable biodegradable medical device of claim 7, wherein a duration of the degradation of the at least one inert layer in response to the introduction of the chemical agent ranges from 1 day to 365 days.

11. The implantable biodegradable medical device of claim 1, wherein the plurality of layers have a thickness ranging from 50 micron to 200 micron.

12. The implantable biodegradable medical device of claim 11, wherein the plurality of layers have varying thickness.

13. The implantable biodegradable medical device of claim 1, wherein the at least one biodegradable material present in the plurality of layers is selected from the group consisting of a polymer, a co-polymer, a homopolymer, an ester, an anhydride, an orthoester, an amide, a polyester, biodegradable linear aliphatic polyesters, biodegradable copolymers between linear aliphatic polyesters, polyanhydrides, poly(orthoesters), poly(ester-ethers), biodegradable polysaccharides, polyamino acids, and inorganic biodegradable polymers.

14. The implantable biodegradable medical device of claim 13, wherein the at least one biodegradable material present in the plurality of layers is selected from the group consisting of polyesters composed of homopolymers or co-polymers of glycolide and lactide,
co-polymers of trimethylene carbonate, e-caprolactone and polydiaxanone, polyglycolic acid (PGA), poly(lactic-co-glycolic acid) (PLGA), poly(ethylene glycol) (PEG), polyglactin, polyglyconate, polydiaxanone, polyglecaprone, polyglycolide, polylactide, polyhydroxybutyrate, poly(glycolide-E-caprolactone), poly (glycolide trimethylene carbonate), poly(L-lactic acide-L-lysine) copolymer, tyrosine-based polyarylates, polyiminocarbonates, polycarbonates, poly(D,L-lactide-urethane), poly(esteramide), poly-P-dioxanone, hyaluronic acid, chitin, chitosan, poly-L-glutamic acid, poly-L-lysine, polyphosphazene and poly[bis(carboxylatophenoxy)phosphazene].

15. The implantable biodegradable medical device of claim 13, wherein a glass transition temperature of the at least one biodegradable material for forming the plurality of layers ranges from 300 degrees C. to 1200 degrees C.

16. The implantable medical device of claim 15, wherein at least one layer of the plurality of layers degrades based on a glass transition temperature associated with at least one biodegradable material composed in the at least one layer.

17. The implantable biodegradable medical device of claim 1, wherein the at least one drug is selected from the group consisting of an anti-inflammatory agent, an anti-thrombotic agent, an anti-proliferative agent, estrogens, a thrombolytic agent, an antimitotic, a smooth muscle cell inhibitor, a fibrinolytic, a anti-antigenic agent, a healing promoter, an antibiotic, a protease inhibitor, one or more antibodies, an anti-mitotic agent, an immunosuppressive agent, a cytostatic agent, a cytotoxic agent, a calcium channel blocker, an antioxidant, and an anti-platelet aggregating agent.

18. The implantable biodegradable medical device of claim 1, wherein the at least one drug is selected from the group consisting of a paclitaxel, a sirolimus, analogs of mitomycin, a dexamethasone, a genistine, flavonoids, flavanones, neoflavones, aurones, chalcones, dihydrochalcones, flavonols, dihydroflavonols, flavones, flavanols, isoflavones, anthocyanidins, proanthocyanidins, isoflavanes, a heparin, a beta-estradiol, analogs of rapamycin, an everolimus, a biolimus, and a zotarolimus.

\* \* \* \* \*